(12) United States Patent
Vogel et al.

(10) Patent No.: US 9,017,710 B2
(45) Date of Patent: *Apr. 28, 2015

(54) INJECTABLE AND SWELLABLE MICROSPHERES FOR TISSUE BULKING

(75) Inventors: Jean-Marie Vogel, Lincoln, MA (US); Egisto Boschetti, Croissy (FR); Richard Thomas, Lincoln, MA (US)

(73) Assignee: Biosphere Medical, Inc., South Jordan, UT (US)

( * ) Notice: Subject to any disclaimer, the term of this patent is extended or adjusted under 35 U.S.C. 154(b) by 399 days.

This patent is subject to a terminal disclaimer.

(21) Appl. No.: 12/197,187

(22) Filed: Aug. 22, 2008

(65) Prior Publication Data

US 2009/0186094 A1   Jul. 23, 2009

Related U.S. Application Data

(63) Continuation of application No. 09/528,989, filed on Mar. 20, 2000, now abandoned.

(51) Int. Cl.
| | |
|---|---|
| *A61F 2/00* | (2006.01) |
| *A61K 9/14* | (2006.01) |
| *A01N 65/00* | (2009.01) |
| *A61L 27/38* | (2006.01) |
| *A61L 27/50* | (2006.01) |
| *A61L 31/00* | (2006.01) |
| *A61L 31/14* | (2006.01) |
| *A61K 31/78* | (2006.01) |
| *A61K 31/785* | (2006.01) |

(52) U.S. Cl.
CPC ............... *A61K 9/14* (2013.01); *A61L 27/3804* (2013.01); *A61L 27/3839* (2013.01); *A61L 27/50* (2013.01); *A61L 31/005* (2013.01); *A61L 31/14* (2013.01); *A61L 2400/06* (2013.01); *A61K 31/78* (2013.01); *A61K 31/785* (2013.01)

(58) Field of Classification Search
CPC ..... A61L 27/50; A61L 27/3804; A61L 31/14; A61K 9/14
USPC .......................................... 424/423, 489, 93.7
See application file for complete search history.

(56) References Cited

U.S. PATENT DOCUMENTS

| | | |
|---|---|---|
| 3,223,083 A | 12/1965 | Cobey |
| 3,900,378 A | 8/1975 | Yen et al. |
| 3,919,411 A | 11/1975 | Glass |
| 4,192,784 A | 3/1980 | Brown et al. |
| 4,197,846 A | 4/1980 | Bucalo |
| 4,213,962 A | 7/1980 | Miura et al. |
| 4,413,070 A | 11/1983 | Rembaum |
| 4,452,916 A | 6/1984 | Boschetti |
| 4,500,658 A | 2/1985 | Fox |
| 4,525,358 A | 6/1985 | Baltes |
| 4,622,362 A | 11/1986 | Rembaum |
| 4,786,555 A | 11/1988 | Howard, Jr. |
| 4,803,075 A | 2/1989 | Wallace |
| 4,999,188 A | 3/1991 | Solodovnik et al. |
| 5,007,940 A | 4/1991 | Berg |
| 5,158,573 A | 10/1992 | Berg |
| 5,202,352 A | 4/1993 | Okada et al. |
| 5,226,914 A | 7/1993 | Caplan |
| 5,298,570 A | 3/1994 | Tahara |
| 5,306,500 A | 4/1994 | Rhee |
| 5,324,775 A | 6/1994 | Rhee |
| 5,336,263 A | 8/1994 | Ersek |
| 5,344,452 A | 9/1994 | Lemperle |
| 5,358,502 A | 10/1994 | Herbig et al. |
| 5,451,406 A | 9/1995 | Lawin |
| 5,470,911 A | 11/1995 | Rhee |
| 5,550,187 A * | 8/1996 | Rhee et al. .................... 525/54.1 |
| 5,550,188 A | 8/1996 | Rhee |
| 5,578,709 A | 11/1996 | Woiszwillo |
| 5,633,001 A | 5/1997 | Agerup |
| 5,635,215 A * | 6/1997 | Boschetti et al. ............. 424/501 |
| 5,648,100 A | 7/1997 | Boschetti |
| 5,667,778 A * | 9/1997 | Atala ............................ 424/93.7 |
| 5,670,177 A | 9/1997 | Briend et al. |
| 5,695,480 A | 12/1997 | Evans et al. |
| 5,716,404 A | 2/1998 | Vacanti |
| 5,792,478 A | 8/1998 | Lawin |
| 5,798,096 A * | 8/1998 | Pavlyk ........................ 424/78.35 |
| 5,830,708 A | 11/1998 | Naughton |
| 5,843,987 A | 12/1998 | Rajagopalan |
| 5,855,610 A | 1/1999 | Vacanti |
| 5,855,615 A | 1/1999 | Bley |
| 5,885,829 A | 3/1999 | Mooney |
| 5,906,934 A | 5/1999 | Grande |
| 5,919,707 A | 7/1999 | Banks |
| 5,922,025 A * | 7/1999 | Hubbard ....................... 424/423 |
| 5,981,825 A | 11/1999 | Brekke |
| 5,992,025 A | 11/1999 | Fricke |
| 6,086,863 A | 7/2000 | Ritter |
| 6,214,331 B1 | 4/2001 | Vanderhoff |
| 6,224,893 B1 | 5/2001 | Langer et al. |

(Continued)

FOREIGN PATENT DOCUMENTS

| | | |
|---|---|---|
| EP | 0251695 A2 | 1/1988 |
| EP | 0648480 | 4/1995 |

(Continued)

OTHER PUBLICATIONS

English translation of WO 89/07455 (machine translation).*

(Continued)

*Primary Examiner* — Shengjun Wang

(74) *Attorney, Agent, or Firm* — Stoel Rives LLP

(57) ABSTRACT

The present invention relates to injectable compositions comprising biocompatible, swellable, hydrophilic, non-toxic and substantially spherical microspheres useful for tissue bulking. The invention also relates to methods of tissue bulking, particularly for the treatment of Gastro-esophageal reflux disease, urinary incontinence, or urinary reflux disease, using the injectable compositions.

26 Claims, No Drawings

(56) References Cited

U.S. PATENT DOCUMENTS

| | | | |
|---|---|---|---|
| 6,335,028 B1* | 1/2002 | Vogel et al. | 424/422 |
| 6,436,424 B1 | 8/2002 | Vogel | |
| 6,660,301 B1 | 12/2003 | Vogel | |
| 6,680,046 B1 | 1/2004 | Boschetti | |
| 6,790,456 B2 | 9/2004 | Vogel | |
| 6,911,219 B2 | 6/2005 | Matson | |
| 7,060,298 B2* | 6/2006 | Vogel et al. | 424/489 |
| 7,338,657 B2 | 3/2008 | Vogel | |
| 7,591,993 B2 | 9/2009 | Boschetti | |
| 8,142,815 B2 | 3/2012 | Vogel et al. | |
| 8,658,215 B2 | 2/2014 | Vogel et al. | |
| 2002/0068089 A1 | 6/2002 | Vogel et al. | |
| 2002/0187172 A1 | 12/2002 | Reb et al. | |
| 2003/0211083 A1 | 11/2003 | Vogel et al. | |
| 2003/0211165 A1 | 11/2003 | Vogel | |
| 2003/0212002 A1 | 11/2003 | Haskell-Luevano et al. | |
| 2004/0091425 A1 | 5/2004 | Boschetti | |
| 2004/0096514 A1 | 5/2004 | Vogel | |
| 2005/0025708 A1 | 2/2005 | Vogel et al. | |
| 2005/0158393 A1 | 7/2005 | Reb | |
| 2006/0039896 A1 | 2/2006 | Kleinsek et al. | |
| 2006/0063732 A1 | 3/2006 | Vogel | |
| 2006/0251582 A1 | 11/2006 | Reb | |
| 2008/0033366 A1 | 2/2008 | Matson | |
| 2008/0039890 A1 | 2/2008 | Matson | |
| 2008/0118569 A1 | 5/2008 | Vogel | |
| 2008/0220077 A1 | 9/2008 | Vogel | |
| 2009/0117196 A1 | 5/2009 | Boschetti | |
| 2009/0186094 A1 | 7/2009 | Vogel | |
| 2010/0119572 A1 | 5/2010 | Boschetti | |
| 2011/0033508 A1 | 2/2011 | Vogel | |
| 2011/0182998 A1 | 7/2011 | Reb | |

FOREIGN PATENT DOCUMENTS

| | | | |
|---|---|---|---|
| EP | 0648480 A2 | | 4/1995 |
| EP | 0713707 A1 | | 5/1996 |
| EP | 0 811373 | * | 6/1997 |
| EP | 0811373 A2 | | 12/1997 |
| FR | 2378808 A1 | | 8/1978 |
| FR | 2784580 | | 4/2000 |
| GB | 2 144 327 A | | 3/1985 |
| JP | 6056676 | | 3/1994 |
| WO | WO 89/07455 | * | 8/1989 |
| WO | WO 89/07455 A1 | | 8/1989 |
| WO | WO 92/06702 A1 | | 4/1992 |
| WO | WO 92/21327 | | 12/1992 |
| WO | WO 93/15721 | | 8/1993 |
| WO | WO 94/21299 | | 9/1994 |
| WO | WO 94/21299 A1 | | 9/1994 |
| WO | WO 96/12510 A1 | | 5/1996 |
| WO | WO 96/039464 | | 12/1996 |
| WO | WO 98/52543 | | 11/1998 |
| WO | WO 99/31167 | | 6/1999 |
| WO | WO 99/34829 | | 7/1999 |
| WO | WO 99/44643 | | 9/1999 |
| WO | WO 00/23054 | | 4/2000 |
| WO | WO 2010/062678 | | 6/2010 |

OTHER PUBLICATIONS

Shafik "Intraesophageal polytef injection for the treatment of reflux esphagitis." Surgical Endoscopy, 1996, vol. 10, No. 3, pp. 329-331.*
Jiaqi, "A New Embolic Material: Super Absorbent Polymer (SAP) Microsphere and its Embolic Effects," *Nippon Acta Radiologica* 56(1):19-24 (1996) [Japanese].
Jiaqi, "A New Embolic Material: Super Absorbent Polymer (SAP) Microsphere and its Embolic Effects," *Nippon Acta Radiologica* 56(1):19-24 (1996) [English Translation].
Shafik, "Intraesophageal polytef injection for the treatment of reflus esphagitis" Surgical Endoscopy 10:329-331 (1996).
U.S. Appl. No. 12/009,181 (U.S. Publ. No. 2008/0118569); Office Action Dated Apr. 4, 2011.
U.S. Appl. No. 08/150,148 (U.S. Patent No. 5,635,215) Office Action Dated Nov. 30, 1995.
U.S. Appl. No. 08/150,148 (U.S. Patent No. 5,635,215) Office Action Dated Jun. 3, 1996.
U.S. Appl. No. 08/150,148 (U.S. Patent No. 5,635,215) Notice of Allowability Dated Sep. 20, 1996.
U.S. Appl. No. 08/471,303; (U.S. Patent No. 5,648,100) Office Action Dated Oct. 16, 1995.
U.S. Appl. No. 08/471,303; (U.S. Patent No. 5,648,100) Office Action Dated May 7, 1996.
U.S. Appl. No. 08/471,303; (U.S. Patent No. 5,648,100) Notice of Allowability Dated Dec. 23, 1996.
U.S. Appl. No. 09/263,773; (U.S. Patent No. 6,335,028) Office Action Dated Jul. 19, 2000.
U.S. Appl. No. 09/263,773; (U.S. Patent No. 6,335,028) Office Action Dated Apr. 20, 2001.
U.S. Appl. No. 09/263,773; (U.S. Patent No. 6,335,028) Notice of Allowability Dated Aug. 17, 2001.
U.S. Appl. No. 09/419,114; (U.S. Patent No. 6,680,046) Office Action Dated Oct. 30, 2001.
U.S. Appl. No. 09/419,114; (U.S. Patent No. 6,680,046) Office Action Dated Jul. 3, 2002.
U.S. Appl. No. 09/419,114; (U.S. Patent No. 6,680,046) Notice of Allowability Dated Jul. 25, 2003.
Hori et al., 'A New Embolic Material: Super Absorbent Polymer (SAP) Microsphere and its Embolic Effects'. IVR, vol. 11, No. 3, pp. 75-81, 1996. With english abstract.
Ott, "Biocompatibility of Microscopic Beads of PMMA (Polymethyl Methacrylate) in Rat Skin," Doctoral Dissertation, Johann Wolfgang Goethe University, Frankfurt am Main, Germany (41 pgs.) (1988).
U.S. Appl. No. 12/695,080, filed Jan. 27, 2010, Reb et al.
U.S. Appl. No. 12/534,070, filed Jul. 31, 2009, Vogel et al.
Appell, "Injectables in the treatment of female stress incontinence" *Curr. Opin. Obstetrics Gynecol.*, 7:393-396 (1995).
Beaujeux, "Trisacryl Gelatin Microspheres for Therapeutic Embolization, II: Preliminary Clinical Evaluation in Tumors and Arteriovenous Malformations" *AJNR* 17(3):541-548 (1996).
Berman, "Comparative Cost Analysis of Collagen Injection and Fascia Lata Sling Cystourethropexy for the Treatment of Type III Incontinence in Women," *J. Urology*, 157:122-124 (1997).
Boschetti, "Synthese et copolymerisation de nouveaux monomeres acryliques diiodes et triiodes," *Bull. Soc. Chim.Fr.*, 4:669-677 (1996) (with English Abstract).
Boschetti, "Polyacrylamide Derivatives to the Service of Bioseparations," *J. Biochem-Biophys. Meth.*, 19:21-36 (1989).
Boschetti, Microspheres for Biochromatography and Biomedical Applications; Part I, Preparation of Microbeads In: Microspheres, Microencapsulation and Liposomes, John Wiley & Sons, Arshady R., Ed. 2: 171-189 (1999).
Brown, "Syntheses and copolymerizations of new water-soluble polyiodinated acrylic monomers," *Makromol. Chem., Rapid Commun.* 6:503-507 (1985).
Cherksey, "Adrenal Chromaffin Cells on Microcarriers Exhibit Enhanced Long-Term Functional Effects When Implanted into the Mammalian Brain," *IBRO*, 657-664 (1996).
Chowdhury., "Use of Microbeads for Cell Transplantation," In: Advanced Research on Animal Cell Technology, A.O.A. Miller ed., Kluwers Acad. Press, 315-327(1989).
Communication Pursuant to Article 96(2) EPC issued on Dec. 3, 2004 in connection with European Application No. 01922415.3.
Dixit, "Hepatocyte immobilization on pHEMA microcarriers and its biologically modified forms" *Cell Transplantation* 1:391-399 (1992).
Edgerton, "Indications for and Pitfalls of Soft Tissue Augmentation with Liquid Silicone" Plast. Reconstr. Surg., 58:157-163 (1976).
Eppley., "A Potential Biomaterial Composite for Dermal and Subcutaneous Augmentation," *Annals of Plastic Surgery*, 32(5):463-468 (1994).
Gerhart, "Biomechanical Optimization of a Model Particulate Composite for Orthopaedic Applications," *Journal of Orthopedic Research*, 4:76-85 (1986).

(56) References Cited

OTHER PUBLICATIONS

Glowacki, "Comparison of Multinucleated Cells Elicited in Rats by Particulate Bone, Polyethylene, or Polymethylmethacrylate," *Journal of Bone and Mineral Research*, 1(4):327-331 (1986).
Goldring, "Multinucleated Cells Elicited in Response to Implants of Devitalized Bone Particles Possess Receptors for Calcitonin," *Journal of Bone and Mineral Research*, 3(1):117-120 (1988).
Goodman, "The Effects of Bulk VERSUS Particulate Polymethylmethacrylate on Bone," *Clin. Orthop. Relat. Res.*, 232:255-262 (1988).
Herschorn, "Followup of Intraurethal Collagen for Female Stress Urinary Incontinence," *J. Urology*, 156:1305-1309 (1996).
Herzog, "Urinary Incontinence: Medical and Psychosocial Aspects," *Ann. Rev. Gerontol. Geriatrics*, 9(Chap. 3):74-119 (1989).
Horak, "Hydrogels in Endovascular Embolization. I. Spherical Particles of Poly(2-hydroethyl methacrylate) and Their Medico-biological Properties" *Biomaterials*, 7:188-192 (1986).
Horak, "Hydrogels in Endovascular Embolization. II. Clinical Use of Spherical Particles" *Biomaterials*, 7:467-470 (1986).
Horak, "Hydrogels in Endovascular Embolization. III. Radiopaque Spherical particles, Their Preparation and Properties" *Biomaterials*, 8:142-144 (1987).
Johnson, "Outcome of Respiratory Symptons After Anti-reflux Surgery on Patients With Gastroesphageal Reflux Disease," *Archives of Surgery*, 131:489-492 (1996).
Khullar, "GAX Collagen in the Treatment of Urinary Incontinence in Elderly Women: A Two Year Follow Up," *British J. Obstetrics & Gynecology*, 104:96-99 (1996).
Klutke, "Early Results With Antegrade Collagen Injection for Post-Radical Prostatectomy Stress Urinary Incontinence," *J. Urology*, 156:1703-1706 (1996).
Kondo, "Bladder Neck Support Prosthesis: A Nonoperative Treatment for Stress or Mixed Urinary Incontinence," *J. Urology*, 157:824-827 (1996).
Krukowski, "Charged Beads Stimulate Bone Formation" 34th Annual Meeting Orth. Res. Soc. (Feb. 1988).
Langer, "Tissue Engineering," *Science*, 260:920-926, May 14, 1993.
Laurent, "Trisacryl Gelatin Microspheres for Therapeutic Embolization, I: Development and In Vitro Evaluation," *Am. J. Neuroradiol.*, 17:533-540 (1996).
Laurent, "Etude Histologique de Plusieurs Materiaux D'Embolisation et D'Un Nouveau Type de Materiel Spherique et Adhesif," *Innov. Tech. Biol. Med. 10*: 358-366 (1989).
Laurent, "Etude Histologique de Plusieurs Materiaux D'Embolisation et D'Un Nouveau Type de Materiel Spherique et Adhesif," *Innov. Tech. Biol. Med. 10*: 358-366 (1989). (English-language Translation).
Leonard, "Treatment of Urinary Incontinence in Children by Endoscopically Directed Bladder Neck Injection of Collagen," *J. Urology*, 156:637-641 (1996).
Lemperle, "PMMA Microspheres for Intradermal Implantation: Part I. Animal Research," *Ann Plast Surg*, 26:57-63 (1991).
Lemperle, "PMMA-Microspheres (Artecoll) for Long-Lasting Correction of Wrinkles: Refinements and Statistical Results," *Aesthetic Plastic Surgery*, 22:356-365 (1998).
Lemperle, "Soft Tissue Augmentation with Artecoll: 10-Year History, Indications, Techniques, and Complications," *Dermatol Surg*, 29:573-587 (2003).
Levesque, "Ten-Year Experience With the Artificial Urinary Sphincter in Children," *J. Urology*, 156:625-628 (1996).
Levine, "Microcarrier Cell Culture: New Methods for Research-Scale Application," *Somatic Cell Genetics*, 3:149-155 (1977).
Lima, "Combined use of enterocystoplasty and a new type of artificial sphincter in the treatment of urinary incontinence," *J. Urology* 156:622-624 (1996).
Mazza, "Polymer Design in Dye Chromatography: From the definition of monomers to the evaluation of polymeric supports," in Protein-Dye Interactions: Developments and Applications, Vijayalakshmi M.A. ed., Elsevier Appl. Sciences, Elsevier Sci. Publ. Ltd., pp. 126-136 (1989).

McClelland, "Evaluation of Antibody Class in Response to Bovine Collagen Treatment in Patients With Urinary Incontinence," *J. Urology*155:2068-2073 (1996).
Millikan, "Long Term Safety and Efficiency with Fibrel in the Treatment of Cutaneous Scars", *J Dermatol Surg Oncol*, 15:837-846 (1989).
Morhenn, "Phagocytosis of Different Particulate Dermal Filler Substances by Human Macrophages and Skin Cells," *Dermatol Surg*, 28:484-490 (2002).
Nebel, "Symptomatic Gastroesophageal Reflux: Incidence and Precipitating Factors," *Am. J. Dig. Dis.*, 21,(11):953-956 (1976).
Obrenovitch, "Microcarrier Culture of Fibroblastic Cells on Modified Trisacryl Beads," *Biol. Cell.*, 46:249-256 (1983).
Owen, "Marrow Stromal Stem Cells," *J Cell Sci. Suppl.*, 10:63-76, 1988.
Perez, "Submucosal Bladder Neck Injection of Bovine Dermal Collagen for Stress Urinary Incontinence in the Pediatric Population," *J. Urology*, 156:633-636 (1996).
Remacle, "Cultures of Preadipocytes on Microparticles Their Properties of Adhesion Proliferation and Differentation," *Manuscript from University Catholique de Louvain, Laboratiore de Biologie Cellulaire*, 1-33 (1997).
Reynolds, "Influence of pathophysiology, severity, and cost on the medical management of gastroesophageal reflux disease," *Am. J. Health-Sys. Pharm.* 53:S5-S12 (1996).
Stinson, "Tissue Reaction Induced in Guinea-Pigs by Particulate Polymethylmethacrylate, Polythene and Nylon of the Same Size Range," *British Jour. Exp. Pathology*, 46:135-146 (1964).
Tuncel, "Nonswellable and swellable ethylene glycol dimethacrylate-acrylic acid copolymer microspheres" *J. Polymer Sci.: Pt. A: Polymer Chem.* 34:45-55 (1996).
Van Wezel, "Growth of Cell-strains and Primary Cells on Microcarriers in Homogeneous Culture," *Nature*, 216:64-65 (1967).
Wein, "Pharmacology of Incontinence," *Urol. Clin. N. Am.*, 22:557-573 (1995).
U.S. Appl. No. 09/528,990: (U.S. Patent No. 6,436,426) Office Action Dated Mar. 22, 2001.
U.S. Appl. No. 09/528,990: (U.S. Patent No. 6,436,426) Office Action Dated Oct. 29, 2001.
U.S. Appl. No. 09/528,990; (U.S. Patent No. 6,436,426) Interview Summary Dated Apr. 4, 2002.
U.S. Appl. No. 09/528,990; (U.S. Patent No. 6,436,426) Notice of Allowability Dated Apr. 9, 2002.
U.S. Appl. No. 09/528,990; (U.S. Patent No. 6,436,426) Supplemental Notice of Allowability Dated May 13, 2002.
U.S. Appl. No. 09/528,989; Office Action Dated Apr. 11, 2001.
U.S. Appl. No. 09/528,989; Office Action Dated Sep. 24, 2001.
U.S. Appl. No. 09/528,989; Office Action Dated Feb. 12, 2003.
U.S. Appl. No. 09/528,989; Office Action Dated Nov. 26, 2003.
U.S. Appl. No. 09/528,989; Notice of Allowability Dated Dec. 7, 2004.
U.S. Appl. No. 09/528,989; Office Action Dated Sep. 19, 2005.
U.S. Appl. No. 09/528,989; Office Action Dated Jan. 19, 2007.
U.S. Appl. No. 09/528,989; Office Action Dated Sep. 20, 2007.
U.S. Appl. No. 09/528,989; Office Action Dated Feb. 27, 2008.
U.S. Appl. No. 09/528,991; (U.S. Patent No. 6,660,301) Office Action Dated Aug. 27, 2001.
U.S. Appl. No. 09/528,991; (U.S. Patent No. 6,660,301) Office Action Dated May 21, 2002.
U.S. Appl. No. 09/528,991; (U.S. Patent No. 6,660,301) Notice of Allowability Dated Jul. 2, 2003.
U.S. Appl. No. 10/220,984; (U.S. Patent No. 7,338,657) Office Action Dated Aug. 24, 2005.
U.S. Appl. No. 10/220,984; (U.S. Patent No. 7,338,657) Office Action Dated Apr. 18, 2006.
U.S. Appl. No. 10/220,984; (U.S. Patent No. 7,338,657) Office Action Dated Jan. 10, 2007.
U.S. Appl. No. 10/220,984; (U.S. Patent No. 7,338,657) Notice of Allowability Dated Oct. 18, 2007.
U.S. Appl. No. 10/029,294; (U.S. Patent No. 7,060,298) Office Action Dated May 19, 2003.
U.S. Appl. No. 10/029,294; (U.S. Patent No. 7,060,298) Office Action Dated Mar. 24, 2004.

(56) References Cited

OTHER PUBLICATIONS

U.S. Appl. No. 10/029,294; (U.S. Patent No. 7,060,298) Office Action Dated Jan. 6, 2005.
U.S. Appl. No. 10/029,294; (U.S. Patent No. 7,060,298) Office Action Dated Aug. 23, 2005.
U.S. Appl. No. 10/029,294; (U.S. Patent No. 7,060,298) Notice of Allowability Dated Feb. 1, 2006.
U.S. Appl. No. 10/222,819; (U.S. Patent No. 6,790,456) Notice of Allowability Dated May 6, 2004.
U.S. Appl. No. 10/704,919; (U.S. Publ. No. 2004/0096514) Office Action Dated Mar. 19, 2007.
U.S. Appl. No. 10/704,919; (U.S. Publ. No. 2004/0096514) Office Action Dated Jan. 9, 2008.
U.S. Appl. No. 10/704,919; (U.S. Publ. No. 2004/0096514) Office Action Dated May 14, 2008.
U.S. Appl. No. 10/704,919; (U.S. Publ. No. 2004/0096514) Office Action Dated Feb. 3, 2009.
U.S. Appl. No. 10/704,919; (U.S. Publ. No. 2004/0096514) Notice of Abandonment and Interview Summary Dated Feb. 3, 2009.
U.S. Appl. No. 10/919,257 (U.S. Publ. No. 2005/0025708) Office Action Dated Oct. 31, 2008.
U.S. Appl. No. 10/919,257 (U.S. Publ. No. 2005/0025708) Office Action Dated Aug. 4, 2009.
U.S. Appl. No. 10/919,257 (U.S. Publ. No. 2005/0025708) Office Action Dated Mar. 16, 2010.
U.S. Appl. No. 10/919,257 (U.S. Publ. No. 2005/0025708) Office Action Dated Oct. 1, 2010.
U.S. Appl. No. 12/534,070 Office Action Dated Dec. 21, 2010.
Chowdhury R. et al., In: Advanced Research on Animal Cell Technology, A.O.A. Miller ed., Kluwers Acad. Press, 315-327 (1989).
U.S. Appl. No. 09/528,990; (U.S. Patent No. 6,436,426) Supplemental Notice of Availability Dated May 13, 2002.
U.S. Appl. No. 09/945,793; (U.S. Publ. No. 2002/0187172) Office Action Dated Jan. 29, 2003.
U.S. Appl. No. 09/945,793; (U.S. Publ. No. 2002/0187172) Office Action Dated Jul. 21, 2003.
U.S. Appl. No. 09/945,793; (U.S. Publ. No. 2002/0187172) Office Action Dated Apr. 29, 2004.
U.S. Appl. No. 09/945,793; (U.S. Publ. No. 2002/0187172) Interview Summary Dated Dec. 22, 2004.
U.S. Appl. No. 10/133,177; (U.S. Patent No. 6,911,219) Office Action Dated Aug. 2, 2004.
U.S. Appl. No. 10/133,177; (U.S. Patent No. 6,911,219) Notice of Allowability Dated Feb. 18, 2005.
U.S. Appl. No. 10/220,982; (U.S. Publ. No. 2003/0211165) Office Action Dated Jul. 15, 2005.
U.S. Appl. No. 10/220,982; (U.S. Publ. No. 2003/0211165) Office Action Dated Jan. 20, 2006.
U.S. Appl. No. 10/220,982; (U.S. Publ. No. 2003/0211165) Office Action Dated Aug. 1, 2006.
U.S. Appl. No. 10/220,982; (U.S. Publ. No. 2003/0211165) Office Action Dated Jun. 11, 2007.
U.S. Appl. No. 10/220,982; (U.S. Publ. No. 2003/0211165) Office Action Dated Oct. 12, 2007.
U.S. Appl. No. 10/220,982; (U.S. Publ. No. 2003/0211165) Office Action Dated Mar. 21, 2008.
U.S. Appl. No. 10/220,982; (U.S. Publ. No. 2003/0211165) Office Action Dated Nov. 18, 2008.
U.S. Appl. No. 10/220,982; (U.S. Publ. No. 2003/0211165) Office Action Dated Aug. 13, 2009.
U.S. Appl. No. 10/220,982; (U.S. Publ. No. 2003/0211165) Office Action Dated Jan. 29, 2010.
U.S. Appl. No. 10/220,983; (U.S. Publ. No. 2003/0212022) Office Action Dated Mar. 18, 2004.
U.S. Appl. No. 10/220,983; (U.S. Publ. No. 2003/0212022) Office Action Dated Sep. 9, 2004.
U.S. Appl. No. 10/220,983; (U.S. Publ. No. 2003/0212022) Office Action Dated Mar. 9, 2005.
U.S. Appl. No. 10/692,785; (U.S. Publ. No. 2004/0091425) Office Action Dated Nov. 16, 2005.
U.S. Appl. No. 10/692,785; (U.S. Publ. No. 2004/0091425) Office Action Dated Jun. 2, 2006.
U.S. Appl. No. 10/692,785; (U.S. Publ. No. 2004/0091425) Office Action Dated Oct. 30, 2006.
U.S. Appl. No. 10/692,785; (U.S. Publ. No. 2004/0091425) Interview Summary Dated Nov. 21, 2006.
U.S. Appl. No. 10/692,785; (U.S. Publ. No. 2004/0091425) Office Action Dated Jul. 12, 2007.
U.S. Appl. No. 10/692,785; (U.S. Publ. No. 2004/0091425) Office Action Dated Jan. 24, 2008.
U.S. Appl. No. 10/692,785; (U.S. Publ. No. 2004/0091425) Office Action Dated Sep. 4, 2008.
U.S. Appl. No. 10/692,785; (U.S. Publ. No. 2004/0091425) Notice of Allowability Dated Sep. 29, 2008.
U.S. Appl. No. 11/030,182; Office Action Dated Nov. 18, 2005.
U.S. Appl. No. 11/030,182; Interview Summary Dated Jun. 29, 2006.
U.S. Appl. No. 11/253,435; (U.S. Publ. No. 2006/0063732) Office Action dated Apr. 6, 2007.
U.S. Appl. No. 11/253,435; (U.S. Publ. No. 2006/0063732) Office Action dated Feb. 26, 2008.
U.S. Appl. No. 11/253,435; (U.S. Publ. No. 2006/0063732) Office Action dated Nov. 18, 2008.
U.S. Appl. No. 11/253,435; (U.S. Publ. No. 2006/0063732) Office Action dated Sep. 14, 2009.
U.S. Appl. No. 11/253,435; (U.S. Publ. No. 2006/0063732) Office Action dated Apr. 8, 2010.
U.S. Appl. No. 11/430,789; (U.S. Publ. No. 2006/0251582) Office Action dated Jan. 23, 2008.
U.S. Appl. No. 11/430,789; (U.S. Publ. No. 2006/0251582) Office Action dated Sep. 12, 2008.
U.S. Appl. No. 11/430,789; (U.S. Publ. No. 2006/0251582) Office Action dated Aug. 17, 2009.
U.S. Appl. No. 11/430,789; (U.S. Publ. No. 2006/0251582) Office Action dated Apr. 14, 2010.
U.S. Appl. No. 11/669,127 (U.S. Publ. No. 2008/0039890); Office Action dated May 12, 2010.
U.S. Appl. No. 12/348,867; (U.S. Publ. No. 2009/0117196) Office Action dated Jul. 23, 2009.
U.S. Appl. No. 12/348,867; (U.S. Publ. No. 2009/0117196) Notice of Allowance dated Dec. 7, 2009.
Notice of Abandonment dated Oct. 16, 2008 for U.S. Appl. No. 09/528,989.
Office Action dated Jun. 13, 2011 for U.S. Appl. No. 10/919,257.
Notice of Allowance dated Sep. 29, 2011 for U.S. Appl. No. 10/919,257.
Notice of Allowance dated Jan. 9, 2012 for U.S. Appl. No. 10/919,257.
Office Action dated Apr. 4, 2011 for U.S. Appl. No. 12/009,181.
Office Action dated Dec. 21, 2010 for U.S. Appl. No. 12/534,070.
Office Action dated Jun. 8, 2011 for U.S. Appl. No. 12/534,070.
Office Action dated Sep. 24, 2001 for U.S. Appl. No. 09/528,989.
Office Action dated Apr. 10, 2006 for U.S. Appl. No. 09/528,989.
Jayakrishnan et al., 'Hydrogel Microspheres from Crosslinked Poly(methyl methacrylate): Synthesis and Biocompatibility Studies', Bull Mater Sci, vol. 12 No. 1, pp. 17-28, Mar. 1989.
Office Action dated Sep. 16, 2013 for U.S. Appl. No. 12/009,181.
Notice of Allowance dated Oct. 11, 2013 for U.S. Appl. No. 13/961,674.
Office Action dated Dec. 5, 2013 for U.S. Appl. No. 13/962,025.
Office Action dated Dec. 20, 2013 for U.S. Appl. No. 14/075,536.
Office Action dated Mar. 6, 2014 for U.S. Appl. No. 12/534,070.
Stenberg et al., 'A new Bioimplant for the Endoscopic Treatment of Vesicoureteral Reflux: Experimental and Short-Term Clinical Results', J Urol Aug. 1995, 154(2pt2): 800:3.
Parulkar et al., 'Dextranomer Dressing in the Treatment of Infected Wounds and Cataneous Ulcers', JPGM, 1995, vol. 31, Issue 1, pp. 28-33.
Notice of Allowance dated Apr. 14, 2014 for U.S. Appl. No. 12/009,181.
Miyake et al., 'Sustained Decrease in Brain Regional Blood Flow After Microsphere Embolism in Rats', Stroke 24:415-420, 1993.
Office Action dated Jun. 6, 2014 for U.S. Appl. No. 14/075,536.
Office Action dated Jun. 17, 2014 for U.S. Appl. No. 13/962,025.
Notice of Allowance dated Nov. 4, 2014 for U.S. Appl. No. 13/962,025.

(56) References Cited

OTHER PUBLICATIONS

Office Action dated Nov. 14, 2014 for U.S. Appl. No. 12/534,070.
Office Action dated Dec. 3, 2014 for U.S. Appl. No. 14/075,536.

Dion et al., 'Dextran Microsphere Embolization: Experimental and Clinical Experience with Radiologic-Pathologic Correlation. Work in Process', RSNA Radiology, Sep. 1986.

* cited by examiner

INJECTABLE AND SWELLABLE MICROSPHERES FOR TISSUE BULKING

CROSS REFERENCE TO RELATED APPLICATIONS

This application is a continuation of U.S. patent application Ser. No. 09/528,989, filed Mar. 20, 2000 (abandoned), which is incorporated herein by reference in its entirety.

1. FIELD OF INVENTION

The present invention relates to tissue bulking, particularly for the treatment of gastro-esophageal reflux disease, urinary incontinence, or urinary reflux disease, using injectable compositions comprising swellable hydrophilic microspheres.

2. BACKGROUND OF THE INVENTION

2.1 Gastro-esophageal Reflux Disease ("GERD")

Although Gastro-esophageal reflux is a normal physiological phenomenon, in some cases it is a pathophysiological situation that can result in a variety of symptoms which may become severe in extreme cases. Gastro-Esophageal Reflux Disease ("GERD"), describes a backflow of acidic and enzymatic liquid from the stomach to the esophagus. It causes burning sensations behind the sternum that may be accompanied by regurgitation of gastric acid into the mouth or even the lung. Complications of GERD which define the severity of the disease include esophageal tissue erosion, and esophageal ulcer wherein normal epithelium is replaced by a pathological tissue.

Statistical data indicate that about 35% of the American population suffer from heartburn at least once a month and between 5 to 10% once a day. More importantly for this kind of disease about 2% of the American population suffer from GERD based on medical evidence data from endoscopic examination. This disease is related to the age of individuals and seems to increase after 40 years of age. (Nebel O. T. et al., *Am. J. Dig. Dis.,* 21(11):953-956 (1976)).

Normally, after a meal the lower esophageal sphincter remains closed, but in patients with GERD, it relaxes and allows some acidic material to reflux into the esophageal tube as a result of stomach contractions. Actually GERD can be attributed primarily to transient relaxation of the lower esophageal sphincter. In other cases, GERD can be attributed to decreased resting tone of the lower esophageal sphincter or to congenital small dimension of the sphincter itself. Other causes also exist which contribute to varying degrees to the existence and severity of this disease.

In addition, there are external factors that contribute to exacerbate the symptoms of GERD, which conditions include eating fatty foods, caffeine intake, smoking, tight clothing and certain medications. Decrease in salivation can also be a factor that exacerbates GERD, since under normal conditions saliva, which is an alkaline liquid, aids in neutralizing acidic reflux and therefore diminishing the duration of the acidic exposure of the esophagus.

Erythema is one of the first visible signs of GERD, which can be seen by endoscopy. Tissue erosion indicates more advanced disease which can then become deep ulcers and lead to cancer (adenocarcinoma increases in incidence faster than other types of cancer). Diffuse ulceration and specific complications occur in about 3.5% of patients less than 65 years of age with esophageal obstruction, blood loss, and in some cases, perforation. Ulcerative situations not only lead to complications, but they are also more resistant to treatments. Although severe complications are uncommon in young patients, they occur in about 20-30% of patients over 65 (Reynolds J. C, *Am. J. Health-Sys. Pharm* 53 (1996)).

At present, GERD is generally managed by over-the-counter ("OTC") antacids or prescription drugs, including proton pump inhibitors, motility agents and $H_2$ blockers. In addition, a portion of GERD patients require surgical intervention; the most common type of surgery is fundoplication which can be done by conventional surgical techniques, or using laparoscopic techniques. However, fundoplication surgery carries the risk of serious side effects and is only marginally successful in curing GERD. Respiratory symptoms are also associated with GERD in about 50% of patients, and in patients undergoing fundoplication, these respiratory symptoms can even increase (76% reported in a study by Johnson W. E. et al., *Archives of Surgery,* 131:489-492 (1996)).

2.2 Urinary Incontinence and Urinary Reflux Disease

Urinary incontinence is a prevalent problem that affects people of all ages and levels of physical health, both in the community at large and in healthcare settings. Medically, urinary incontinence predisposes a patient to urinary tract infections, pressure ulcers, perineal rashes, and urosepsis. Socially and psychologically, urinary incontinence is associated with embarrassment, social stigmatization, depression, and especially for the elderly, an increased risk of institutionalization (Herzo et al., *Ann. Rev. Gerontol. Geriatrics,* 9:74 (1989)). Economically, the costs are astounding; in the United States alone, over ten billion dollars per year is spent managing incontinence.

Incontinence can be attributed to genuine urinary stress (urethra hypemobility), to intrinsic sphincter deficiency ("ISD"), or both. It is especially prevalent in women, and to a lesser extent incontinence is present in children (in particular, ISD), and in men following radical prostatectomy.

One approach for treatment of urinary incontinence involves administration of drugs with bladder relaxant properties, with anticholinergic medications representing the mainstay of such drugs. For example, anticholinergics such as propantheline bromide, and combination smooth muscle relaxant/anticholinergics such as racemic oxybutynin and dicyclomin, have been used to treat urge incontinence. (See, e.g., A. J. Wein, *Urol. Clin. N. Am.,* 22:557 (1995)). Often, however, such drug therapies do not achieve complete success with all classes of incontinent patients, and often results in the patient experiencing significant side effects.

Besides drug therapies, other options used by the skilled artisan prior to the present invention include the use of artificial sphincters (Lima S. V. C. et al., *J. Urology,* 156:622-624 (1996), Levesque P. E. et al., *J. Urology,* 156:625-628 (1996)), bladder neck support prosthesis (Kondo A. et al., *J. Urology,* 157:824-827 (1996)), injection of crosslinked collagen (Berman C. J. et al., *J. Urology,* 157:122-124 (1997), Perez L. M. et al., *Urology,* 1:633-636 (1996); Leonard M. P. et al., *J. Urology,* 156:637-640 (1996)), and injection of polytetrafluoroethylene (Perez L. M. et al., *J. Urology,* 156:633-636 (1996)).

A recent well known approach for the treatment of urinary incontinence associated with ISD is to subject the patient to periurethral endoscopic collagen injections. This augments the bladder muscle in an effort to reduce the likelihood of bladder leakage or stress incontinence.

Existing solutions to circumvent incontinence have well known drawbacks. The use of artificial sphincters for children with intractable incontinence requires long term surveillance of the urinary tract because of the potential for renal failure after device placement (Levesque P. E. et al., *J. Urology*, 156:625-628 (1996)). While endoscopically directed injections of collagen around the bladder neck has a quite high success rate in sphincter deficiency with no significant morbidity, the use of collagen can result in failures that occur after an average of two years and considerations need to be given to its cost effectiveness (Khullar V. et al., *British J. Obstetrics & Gynecology*, 104:96-99 (1996)). In addition, deterioration of patient continency, probably due to the migration phenomena (Perez L. M. et al.) may require repeated injections in order to restore continency (Herschorn S. et al., *J. Urology*, 156:1305-1309 (1996)).

The results with using collagen following radical prostatectomy for the treatment of stress urinary incontinence have also been generally disappointing (Klutke C. G. et al., *J. Urology*, 156:1703-1706 (1996)). Moreover, one study provides evidence that the injection of bovine dermal collagen produced specific antibodies of IgG and IgA class. (McCelland, M. and Delustro, F., *J. Urology* 155, 2068-2073 (1996)). Thus, possible patient sensitization to the collagen could be expected over the time.

Despite of the limited success rate, transurethral collagen injection therapy remains an acceptable treatment for intrinsic sphincter deficiency, due to the lack other suitable alternatives.

Urinary reflux disease, or "vesicoureteral reflux" in its medical term, simply means that urine goes backwards in the ureters during urination. The disease often occurs in young children. The ureter is the tube which connects the kidneys with the bladder. Urine is supposed to go in one direction: from the kidneys to the bladder. When urine goes up from the bladder to the kidneys, it can result in health problems for the person.

Urinary reflux can lead to kidney damage. Refluxing urine can carry bacteria to the kidney, where it can cause kidney infection. Children with reflux of urine are much more likely to have kidney infection than children who do not have reflux. The combination of reflux and infection can lead to areas of permanent kidney damage or "renal scarring." This scarring is detected by doing an X-ray called an intravenous pyelogram (IVP), or preferably, a renal scan. If it is extensive enough, the scarring can lead to loss of function of one or both kidneys.

The key to preventing renal scarring is preventing kidney infections. This is currently being carried out in two ways. In most cases, long term prophylactic antibiotics are given. The other method of preventing urinary tract infections is surgical correction of the reflux. Both methods, however, have drawbacks. Long term use of antibiotics may cause unpredictable side effects and surgical procedures involve unnecessary risks.

Even though many urinary reflux disease will go away on its own in children, some cases often lead to severe kidney and urinary tract infections and even total kidney failure. There is a need, therefore, for a safe, effective, less intrusive, and long lasting method of treating urinary reflux disease.

2.3 Tissue Bulking

Prior to the present invention, tissue bulking has been used for the treatment of GERD and urinary incontinence. In an attempt to increase the function of the sphincter, bulking methods using liquid or semi-liquid preparation, such as collagen; rigid and non-deformable particles, such as carbon particles; and injectable deformable particles, such as Teflon® paste have been used in patients. These methods have been generally unsuccessful, however, as they present various drawbacks.

Tissue bulking agents are either biologically derived or synthetical and are designed to be injected or implanted in or near the sphincter or bladder neck to increase tissue bulk effect. While bulking procedures are gaining acceptance, biologically-derived bulking agents may be absorbed by the body, requiring repeated treatments. Consequently, they are not considered the definitive treatment for GERD, urinary incontinence, or urinary reflux disease. In addition, physicians have experienced problems with currently available synthetic agents, including movement of the synthetic agents to other non-affected parts of the body causing adverse health effects, incompatibility of the synthetic agents with the human body, and difficulty in injecting the agents into the blood vessels or insufficient mechanical resistance.

Liquid or semi-liquid preparations with various degrees of viscosity have been used for tissue bulking. The best known example is a collagen preparation manufactured by Collagen Corporation (now part of Inamed) and marketed by C. R. Bard. These preparations are easily injectable, but they have on or more of the following limitations: (1) the collagen is gradually displaced within the tissue in which it was originally injected, thereby reduce or eliminating the intended bulking effect; (2) the collagen is digested biologically, through macrophages, or through the lymphatic system; and (3) the collagen tends to form a continuous foreign mass within the sphincter after injection thereof.

Solid rigid non-deformable particles, such as carbon particles, have also been used for tissue bulking. These particles or preparations, however, are either too fragile or too large to be injected, or too small and are digested. Therefore, they all have one or more of the following limitations: (1) the particles are too large to be injected through needles of 18 to 26 gauge, thus limiting their applicability and effectiveness in many tissuing bulking cases; (2) it is difficult to inject the particles through needles of 18 to 26 gauge because their irregular shapes make them clamp together; (3) the particles are fragile so that they break during injection and the fragments are digested; (4) the injected particles are too small and are digested by the lymphatic system; and (5) the injected particles are displaced as they do not adhere to the surrounding cells at the site of injection.

Injectable deformable particles, such as Teflon® particles, have also been used for tissue bulking. However, Teflon® particles have one or more of the following limitations: (1) the particles slide with the tissue and do not stay in place of injection; (2) the particles deform during and after injection, reducing the intended tissue bulking effect; and (3) the particles are digested or eliminated by the lymphatic system partly due to the fact that their diameters become smaller as a result of injection.

Therefore, there is a great need for safe, biocompatible, stable and effective methods of tissue bulking for the treatment of various tissue defects, particularly for the treatment of GERD, urinary incontinence, and urinary reflux disease. There is also a need for stable and biocompatible injectable composition for tissue bulking.

3. SUMMARY OF THE INVENTION

The present invention provides injectable compositions comprising swellable microspheres and method of using the injectable compositions to perform tissue bulking, particularly for treatment of GERD, urinary incontinence, and urinary reflux disease in a mammal. The composition is injectable through 18 to 26 gauge needles and the microspheres are not capable of being eliminated by macrophage (digested) or other elements of said mammal's immune or lymphatic system after injection.

The microspheres of the present invention are highly water absorbing and capable of swelling to many times of their original sizes under certain conditions. The microspheres of the present invention generally comprise crosslinked polymers. Preferably, the microspheres comprise sodium acrylate polymer, acrylamide polymer, acrylamide derivative polymer or copolymer, sodium acrylate and vinyl alcohol copolymer, vinyl acetate and acrylic acid ester copolymer, vinyl acetate and methyl maleate copolymer, isobutylene maleic anhydride crosslinked copolymer, starch-acrylonitrile graft copolymer, crosslinked sodium polyacrylate polymer, crosslinked polyethylene oxide, or mixtures thereof. These microspheres are capable of swelling upon contacting with medium resembling the properties of physiological fluids, thus allowing the microspheres to secure themselves into position after injection into the body. Furthermore, the microspheres are substantially spherical and can be calibrated so that their sizes can be accurately determined. The microspheres of the invention have diameters from about 10 to about 500 µm before swelling. Preferably, before swelling, the diameters of the microspheres are from about 10 to about 300 µm and, most preferably, from about 100 to about 300 µm. After injection and swelling, the microspheres have average diameters larger than about 40 µm, preferably larger than about 70 µm and, more preferably, larger than about 100 µm.

In a preferred embodiment of the present invention, the microspheres further comprise cell adhesion promoters or cells on at least a portion of their surfaces. The cells are preferably autologous cells from the subject mammal. Most preferably, the cells are autologous cells from the same type of tissues being treated, such as fat cells, muscle cells, subcutaneous cells, dermal cells, and epidermal cells.

The microspheres of the present invention may further comprise a therapeutic or prophylactic agent, radio-pacifying agent, contrast agent or other detectable substances, targeting agent, or mixtures thereof, providing therapeutic and other benefits to the skin in addition to tissue bulking.

In a preferred embodiment, the composition of the present invention comprises the microspheres in an amount ranges from about 10% to about 90% by weight and the biocompatible carrier from about 10% to about 90% by weight. Preferably, the injectable composition is a suspension of the microspheres in the biocompatible carrier. The biocompatible carrier of the present invention is preferably a solvent in which the microspheres are suspended. The solvent is preferably in such a condition that the microspheres can be uniformly suspended and, more importantly, that the swelling of the microspheres are also controlled by adjusting the solvent, the salt and ionic concentration, the pH value, or combinations thereof. Suitable solvents for the present invention include aqueous based solutions such as saline solutions, PBS solutions, alcohol based solutions, and other biocompatible hydro-organic solutions known in the art.

The microspheres of the present invention are capable of swelling upon contact with physiological fluids, including blood, and cells and tissues at the injection site. The degree of swelling depends on factors such as the material of the microspheres and the degree of crosslinking, the solvent in which the microspheres were suspended before injection, and the biological and physiological conditions at the site of injection. Therefore, knowing the site of injection and its biological and physiological conditions will allow control of the degree of swelling of the microspheres after injection by selecting the material for microspheres and the solvent in which they are suspended.

In a preferred embodiment, there is no aggregation or clumping of the microspheres in the injectable composition before and during injection. The injectable composition of the invention further comprises a cell adhesion promoter, cells or both associated with the microspheres, including on the surface of the microspheres. In addition, the injectable composition can contain one or more of a therapeutic or prophylactic agent, radiopacifying agent, and contrast agent or medium or other detectable substances to provide therapeutic and other benefits while performing tissue bulking.

The present invention additionally provides methods of tissue bulking and treatment of GERD, urinary incontinence, and urinary reflux disease. Specifically, the invention provides a method of causing tissue bulking in a mammal by administering swellable, hydrophilic, substantially and non-toxic spherical microspheres in a biocompatible carrier to the mammal. The composition is injectable through a needle of about 18 to 26 gauge, preferably about 22 to 24 gauge, and the microspheres are not capable of being digested or eliminated by the lymphatic or immune system.

According to the present invention, a preferred method of administration is injecting the composition into an area of the mammal that is in need of tissue bulking. The tissue bulking method of the present invention is especially suitable for the treatment of GERD, urinary incontinence, and urinary reflux disease. A preferred method of administration is injecting the composition into the walls of the sphincter for treatment of GERD and into the bladder sphincter or the urethra for the treatment of urinary incontinence and urinary reflux disease.

The present invention further provides a method of causing tissue bulking by administering the injectable suspension extracorporeally into organs, components of organs, or tissues prior to the inclusion of said organs, or components of organs into body.

The present invention additionally provides a kit for performing tissue bulking. The tissue bulking kit of the present invention comprises an 18 to 26 gauge needle and a corresponding syringe, wherein the syringe contains a composition comprising biocompatible, swellable, hydrophilic, non-toxic and substantially spherical microspheres and a biocompatible carrier. The composition is injectable through the needle and the microspheres are not capable of being digested or eliminated by macrophage or other elements of said mammal's immune system. Alternatively, the syringe does not contain a solution or suspension but is accompanied by (a) dry microspheres which are ready for preparation of a suspension; (b) a preformed solution or suspension of microspheres; or (c) dry microspheres and a biocompatible solution in separate containers.

4. DETAILED DESCRIPTION OF THE INVENTION

The present invention provides a safe, effective, stable, and long lasting method of tissue bulking, which method is useful for the treatment of a variety of tissue defects. The method is particularly useful for the treatment of Gastro-esophageal reflux disease, urinary incontinence, and urinary reflux disease. The invention encompasses injectable compositions comprising biocompatible, swellable, hydrophilic, non-toxic and substantially spherical microspheres and a biocompatible carrier. The invention further provides methods of tissue bulking by administrating the injectable composition to a mammal in need of treatment for various tissue defects, particularly, Gastro-esophageal reflux disease, urinary incontinence, or urinary reflux disease. The injectable compositions and methods of tissue bulking of the present invention are believed to have the following advantages: (1) the injected materials are not easily displaced within the tissues in which they were originally injected, thus the intended tissue bulking effect is achieved without repeated administration or causing adverse effects to the patient, (2) the injected materials are not readily digested, displaced, or eliminated either biochemically or through the lymphatic system, thus the method is effective and long lasting, (3) the materials are of sufficient size to be injected through 18 to 26 gauge needles, thus the method is accurate, efficacious and less intrusive to the patient, (4) the injected particles are not fragile, facilitating easy injection without being broken, thus providing easy and safe injection, and, preferably, (5) the injected particles are not irregularly shaped and do not clump together, also providing easy and accurate injection. These benefits, whether alone or in combinations, enhance the effectiveness of the treatment and are safe, convenient and comfortable for patients.

As used in the present invention, "microspheres" means polymer or combinations of polymers made into bodies of various sizes. The microspheres can be in any shape, although they are often in substantially spherical shape. Further, as part of the injectable composition of the present invention, the microspheres are also sterilized before injection.

"Swellable" microspheres, as used in the present invention, refers to microspheres that are capable of being enlarged in size, yet still retain substantially the same shape, upon certain conditions such as contacting physiological fluids. Preferably, the swellable microspheres of the present invention can be enlarged to about 15 times of their original sizes. The degree of swelling can be controlled by controlling factors such as the solvents in which they are suspended, specific polymers used to make the microspheres and degree of crosslinking. This property enables the microspheres to be injected through needles of 18 to 26 gauge, yet be enlarged and secured at the injection site and of sufficient size to avoid or reduce the chance of being eliminated by the lymphatic or immune system of the mammal.

"High water absorbing polymers" as used in the present invention refers to polymers that can absorb at least 5% of water by weight or that are capable of increasing their dry weight to about 20 times of their original weight.

"Biodegradable" microspheres refer to microspheres that are capable of being absorbed by the body, chemically, physiologically, or by other biological means, over a period of time.

The microspheres of the present invention also comprise particles that are "hydrophilic," which, as used in the invention, means the particles can dissolve in, absorb, or mix easily with water or aqueous solution.

"Substantially spherical" generally means a shape that is close to a perfect sphere, which is defined as a volume that presents the lowest external surface area. Specifically, "substantially spherical" in the present invention means, when viewing any cross-section of the particle, the difference between the average major diameter and the average minor diameter is less than 20%. The surfaces of the microspheres of the present invention appear smooth under magnification of up to 1000 times. The microspheres of the present invention may comprise, in addition to the particles, other materials as described and defined herein.

"Tissue bulking" in the context of the present invention refers to any change of the natural state of a mammal's non-dermal tissues due to external acts or effects. The tissues encompassed by the invention include, but not limited to, muscle tissues, connective tissues, fats, and, nerve tissues. The tissues encompassed by the present invention may be part of many organs or body parts including, but not limited to, the sphincter, the bladder sphincter and urethra.

"Injectable" as used in the present invention means capable of being administered, delivered or carried into the body via syringe, catheters, needles or other means for injecting or infusing microspheres in a liquid medium.

"Cell adhesion promoter" in the present invention means any material that, because of their presence in or association with the microspheres, promotes or enhances the adhesiveness of cells to the surface of the microspheres. These materials are often proteins that are bound to the surface of the microspheres through covalent bonds of the proteins and the polymers.

"Therapeutic agent" in the present invention refers to any substance that provides therapeutic effects to the process of tissue bulking or biological or physiological responses to the tissue bulking. An example of therapeutic agent is an anti-inflammation agent that prevents or reduce the effect of inflammations associated dermal augmentation.

"Chemical modification" in the present invention means the changes of chemical properties and characteristics of the microspheres, either during their production process or by way of mixing or contacting them with various agents or tissues, such that the microspheres have the ability to perform, in addition to tissue bulking, other functions once injected into the body.

For clarity of disclosure, and not by way of limitation, the detailed description of the present invention is divided into the subsections which follow.

4.1 Microspheres

Microspheres for use in the present invention are based on non-toxic, biocompatible, swellable, hydrophilic, and substantially spherical particles which comprise various polymers. The microspheres of the present invention comprise crosslinked polymers that are high water absorbing and, thus, capable of swelling upon contacting with aqueous medium in certain conditions. As understood by a person skilled in the art, the degree of swelling of crosslinked polymers generally depends on the properties of the polymeric materials such as their ionic character, the hydrophilicity of the polymeric materials, and the degree of crosslinking. Properties, such as salt and ionic concentration and level of pH, of the solvent in which the microspheres are suspended or with which the microspheres are contacting also affect the degree of swelling.

As disclosed herein, by controlling the size and the degree of swelling of certain crosslinked and swellable polymers, safe, effective, and long lasting tissue bulking can be achieved using these microspheres. According to the invention, polymeric materials having high water absorbing ability are first chosen. The swellability of these polymers can be further manipulated by controlling the polymer's ionic character and the degree of crosslinking by methods known to a skilled artisan.

The microspheres of the present invention can be either anionic or cationic. Preferably, cationic microspheres are used because of their superior ability of promoting cell adhesion. The crosslinking degree of the microspheres can be changed either chemically or through radiation. A variety of crosslinking agents may be used, including, but not limited to, tetraethylene glycol diacrylate, tetraethylene glycol dimethacrylate, ethylene glycol dimethacrylate, methacrylate, and pentaerythritol dimethacrylate. The microspheres of the invention may comprise from about 0.5% to about 20%, by molecular weight, of crosslinkers. Preferably, the microspheres comprise from about 1% to about 5%, by molecular weight, of crosslinkers.

More importantly, the present invention has discovered that the swelling of the microspheres comprising these polymers can be further controlled by controlling the solvent in which the microspheres are suspended. This is achieved through two steps as disclosed herein. First, the size of the microspheres before injection are controlled by using appropriate solvents, salt concentration and pH level according to the specific microspheres used. The microspheres before injection may either remain in their original size or swell to certain degree due to their contact with the solvent. The pre-injection swelling is controlled so that the microspheres are injectable through 18 to 26 gauge needles. Second, after injection and upon contacting with tissues at injection site, the microspheres may further swell into predetermined size or retain their pre-injection size, either of which size will allow the microspheres to be secured at the site of injection and achieve desired tissue bulking effect. The degree of pre-injection swelling, and thus the after injection swelling, is determined by the particular microspheres used and the nature and location of the tissue defects being treated.

Microspheres for use in the present invention have diameters range from about 10 to about 500 µm before swelling. Preferably, before swelling, the diameters of the microspheres are from about 10 to about 300 µm and, most preferably, from about 100 to about 300 µm. After injection and swelling, the microspheres have average diameters larger than about 40 µm, preferably larger than about 70 µm and, more preferably, larger than about 100 µm. The microspheres of the present invention are capable of swelling to about 4 times of their original diameters or about 15 times of their original volume. The full swollen size of the microspheres after injection are controlled, by various means discussed above, so that they are secured at the site of injection while not causing any potential injuries to the tissues. Further, the full swollen sizes of the microspheres after injection are predetermined based on factors such as the physiological conditions of the injection site, the original microspheres sizes, the solvent used and the pre-injection swelling of the microspheres. Thus, a specific injection plan can be designed according to the particular tissue bulking need of the case. These sizes and properties of the microspheres are advantageous in that they enable the microspheres to be easily injectable through needles of 18 to 26 gauge, preferably 22 to 24 gauge, yet the microspheres are large enough so that they will be secured at the site of injection and will not be digested or eliminated by macrophage or other elements of the immune or lymphatic system.

The microspheres are also resistant to injection force created by 18 to 26 gauge needles and to the muscle contraction stress generated during and after the injection process. The microspheres are also thermally stable which allows for easy, convenient sterilization, and frozen storage for the preparation of injection.

Many types of crosslinked polymers having high water absorbing ability are suitable for use in the present invention as long as they are non-toxic to tissues and cells and are biocompatible. Preferably, the polymers are selected from the group consisting of sodium acrylate polymer, acrylamide polymers, acrylamide derivative polymers or copolymers, sodium acrylate and vinyl alcohol copolymer, saponification products of copolymer of vinyl acetate and acrylic acid ester, vinyl acetate and acrylic acid ester copolymer, vinyl acetate and methyl maleate copolymer, isobutylene-maleic anhydride crosslinked copolymer, starch-acrylonitrile graft copolymer and its saponification products, crosslinked sodium polyacrylate polymer, and crosslinked polyethylene oxide.

The microspheres of the present invention can be biodegradable or non-biodegradable. Preferably, the microspheres of the invention are sterilized before injection. They are also thermally stable which allows for easy, convenient sterilization, and frozen storage. The microspheres for use in the present invention are also stable in suspension which allows the microparticles to be formulated and stored in suspension and injected with different liquids or oils. More specifically, the hydrophilic nature of the microspheres permits placing them in suspension, and in particular, in sterile form of injectable solutions, while avoiding the formation of aggregates or adhesion to the walls of storage containers and implantation devices, such as catheters, syringes, needles, and the like.

The microspheres of the present invention may contain within their structure or on their surfaces other chemicals, therefore displaying particular properties, such as therapeutic, radio-pacifying, and contrasting effects; promotion of cell adhesion; and capability of being chemically modified.

The microspheres of the present invention may further associated with contrast medium or agent. Contrast media useful within the present invention can be found in Dawson et al. *Contrast Medium in Practice* (Springer-Verlag, 1994). Contrast media include, but not limited to, ultrasonic media, superparamagnetic media, and gadolinium contrast media. Preferably, the contrast media are any media that contain barium or iodine salts, such as high molecular weight salts, including acylamino-e-propion-amido-3-triiodo-2,4,6-benzoic acid, which can be prepared under the conditions described by Boschetti et al. (*Bull. Soc. Chim.*, No. 4 France, (1986)). In the case of barium or magnetite salts, they can be directly introduced in powered form in the initial monomer solution.

In another embodiment of the invention, the microspheres have specific properties suitable for cell adhesion and cells growth promotion, making the microspheres particularly useful for certain tissue bulking procedures. Cells are associated with the microspheres, through adhesion or other means, prior to injection. Preferably, the cells are autologous cells from the subject mammal. These autologous cells are preferably the same type of cells that need to be repaired in the tissue bulking procedure, such as fat cells, muscle cells, subcutaneous cells, dermal cells, epidermal cells, connective tissue cells, or combinations thereof. The autologous cells may also preferably be cells that enhance or promote the growth or connection of cells or tissues, such as fibroblast.

Various types of cell adhesion promoters well known in the art may be used in the present invention. In particular, cell adhesion promoters can be selected from collagen, gelatin, glucosaminoglycans, fibronectins, lectins, polycations (such polylysine, chitosan and the like), extracellular matrix, degradation products of cells or tissues, or any other natural or synthetic biological cell adhesion agent.

Cell adhesion promoters or marking agents are introduced on microspheres by chemical coupling procedures well known in affinity chromatography, referred to by the term "ligand immobilization". Another method of introduction is by diffusion within the gel network that constitutes the bead and then trapping the diffused molecules in place by precipitation or chemical cross-linking. Therapeutic agents, drugs or any other active molecules that are suitable for transportation by the beads can also be introduced into the microspheres prior to injection.

The microspheres of the present invention also can be chemically modified so that they will "carry" therapeutic effects, vascularization effects, anti-vascularization effects, visualization properties, anti-inflammatory effects, anti-bacterial effects, anti-histamine effects, or combinations thereof. The chemical modification of the microspheres of the present invention is made possible by the fact that the microspheres comprise particles made of polymers that are crosslinked so that they can contain chemicals within their structures that possess various properties and that they possess unique characteristics associated with surface covalent bonds.

Incorporation of active molecules, such as drugs, into the microspheres of the present invention can be accomplished by mixing dry microspheres with solutions of said active molecules or drugs in an aqueous or hydro-organic solution. The microspheres swell by adsorbing the solutions and incorporate the active molecule of interest into the microsphere network. The active molecules will remain inside the microsphere due to an active mechanism of adsorption essentially based on ion exchange effect. The microspheres by their nature carry cationic groups and have the ability to adsorb anionic molecules, such as well known anti-inflammatory drugs, and these anionic molecules are then released slowly upon injection into the patient due to the action of physiological salt and pH. The ability of various types of microspheres to adsorb drug molecules may be readily determined by the skilled artisan, and is dependent on the amount of cationic monomers present in the initial solution from which the microspheres are prepared.

Microspheres of the present invention further possess the property of non-aggregating, which usually results from an ionic charge of the microspheres. This allows easier injection and more effective tissue bulking, especially in situations where cells are associated with the microspheres. This property is important to tissue bulking of the present invention because it makes injection of the microspheres through 18 to 26 gauge needles possible and easier. This property of the microspheres also prevents them from aggregating or adhering to syringe or needle walls or other device used in the process.

The microspheres of the invention can be obtained by standard methods of polymerization described in the art such as French Patent 2,378,808 and U.S. Pat. Nos. 5,648,100 and 5,635,215 each of which is incorporated herein by reference. In general, the polymerization of monomers in solution is carried out at a temperature ranging between about 0° C. and about 100° C. and between about 40° C. and about 60° C., in the presence of a polymerization reaction initiator.

Microspheres of the present invention can also be prepared by suspension polymerization, drop-by-drop polymerization or any other method known to the skilled artisan. The mode of microsphere preparation selected will usually depend upon the desired characteristics, such as microsphere diameter and chemical composition, for the resulting microspheres. The microspheres of the present invention can further be made by methods of polymerization described in the art (see, e.g., E. Boschetti, *Microspheres for Biochromatography and Biomedical Applications. Part I, Preparation of Microbeads* In: *Microspheres Microencapsulation and Liposomes*, John Wiley & Sons, Arshady R., Ed., 2:171-189 (1999), which is incorporated herein by reference). Microspheres can also be prepared starting from an aqueous solution of monomers containing adhesion agents such as collagen (gelatin is a denatured collagen). The solution is then mixed with a non-aqueous-compatible solvent to create a suspension of droplets, which are then turned into solid gel by polymerization of monomers by means of appropriate catalysts. Microspheres are then collected by filtration or centrifugation and washed.

4.2 Injectable Composition

The present invention provides an injectable composition suitable for tissue bulking. Specifically, the suspension comprises biocompatible, swellable, hydrophilic, non-toxic, and substantially spherical microspheres and a biocompatible carrier. The composition is injectable through needles of about 18 to 26 gauge, preferably about 22 to 24 gauge, and said microspheres are not capable of being digested or eliminated by macrophage or other elements of said mammal's immune or lymphatic system.

The various specific and preferred embodiments for microspheres described in §4.1 can be used in the injectable composition.

The injectable suspension of the present invention preferably comprises cells. The cells are preferably associated with the microspheres. More preferably, the cells are autologous cells from the subject mammal. These autologous cells are preferably the same type of cells that need to be repaired in the tissue bulking procedure, such as fat cells, muscle cells, subcutaneous cells, dermal cells, epidermal cells, connective tissue cells, or combinations thereof. The autologous cells may also preferably be cells that enhance or promote the growth or connection of cells or tissues, such as fibroblast.

Many types of emulsion and solvents can be used as the biocompatible carrier for the injectable composition. The solvent is preferably in such a condition that the microspheres can be uniformly suspended and, more importantly, that the swelling of the microspheres are also controlled by adjusting the solvent, the salt and ionic concentration, the pH value, or combinations thereof. Suitable solvents for the present invention include aqueous based solutions such as saline solutions, PBS solutions, alcohol based solutions, and other biocompatible hydro-organic solutions known in the art.

Salt concentration and pH level of the solvent are important in controlling the degree of swelling of the microspheres once they are suspended in the solvent. The presence of cations such as sodium, potassium, calcium, magnesium, iron, zinc, and ammonium has various level of effects on the degree of swelling of the microspheres depending on the specific polymer and salt used. The degree of swelling of the microspheres is partially controllable by changing the balance of smaller cations and larger cations between the solvent and the microspheres. In a preferred embodiment, the contrasting agent associated with the microspheres serves as an agent controlling the degree of swelling of the microspheres. A salt level of 0.01 M to 5 M is effective to keep the microspheres from swelling. While the microspheres swell uninhibitedly under a neutral pH level, the change of pH level will affect the degree of swelling. For the anionic microspheres, the preferred pH level to shrink the microspheres or to keep them from swelling is from about 0.1 to 5. For the cationic microspheres, a pH level ranges from about 6 to about 11 will shrink the microspheres or keep them from swelling.

Upon suspension in the solvent and before injection, the microspheres may swell and the degree of swelling is controlled by the solvent and other conditions, such as time and temperature of suspension. The pre-injection swelling of the microspheres is further determined by the desired after-injection-swelling for the microspheres. Thus, microspheres that have obtained high degree of swelling before injection will swell little after injection, whereas microspheres that have swelled little before injection will obtain a higher degree of swelling after injection. The size of the microspheres before, during and after injection is always controlled such that they are easily injectable through 18 to 26 gauge needles yet become secured at the site of injection.

The biocompatible carrier of the present invention can also be an emulsion. In this embodiment, the properties of the microspheres, especially their size and degree of swelling, are preserved through the well controlled balance between the aqueous and the non-aqueous phases in the emulsion.

Preferably, the injectable composition of the present invention comprise the microspheres in an amount from about 10% to about 90% by weight and the biocompatible carrier in an amount from about 10% to about 90% by weight. More preferably, the amount ranges from 10% to 50% by weight for microspheres and from 50% to 90% for biocompatible carrier. The relative amount of the microspheres and the carrier changes according to the need of the specific tissue bulking performed, depending on factors such as size of needle used, type of microspheres and carriers used, type of skin deficiency, area of injection, type of tissue or cells being bulked, and whether cells are associated with the microspheres prior to injection.

To prepare a suspension of the microspheres, dried sterilized microspheres are mixed with the desired solvent at a pre-determined time such that the pre-injection swelling of the microspheres is controlled. The solvent can be pre-sterilized or the suspension of microspheres and the solvent can be sterilized together before injection thereof. Factors such as the material, size and crosslinking degree of the microspheres; the type, volume, salt concentration, pH level and temperature of the solvent; and the time of mixing are all considered before an injectable suspension is made and the injection is carried out thereafter.

The composition of the present invention is easily injectable, through needles of 18 to 26 gauge, preferably, 22 to 24 gauge, into all parts of the mammal in need of treatment without causing significant pain or discomfort. This is due to, among other factors, the size and the physical resiliency of the microspheres, the biocompatible nature of the carrier, and the amount of the composition administered in accordance with the character and location of the tissue defects.

4.3 Method of Tissue Bulking

The present invention further provides methods of causing tissue bulking. The methods comprise administering a composition of biocompatible, swellable, hydrophilic, non-toxic and substantially spherical microspheres in a biocompatible carrier to a mammal. The method further specifies that the suspension is injectable through a needle of about 18 to 26 gauge, preferably about 22 to 24 gauge, and the microspheres are not capable of being digested, displaced, or eliminated by the mammal's lymphatic or immune system.

The various specific and preferred embodiments of the injectable compositions described in §§4.1 and 4.2 can be used in the method for tissue bulking.

The tissue bulking method of the present invention is suitable for the treatment of various tissue defects, such as defects in dental tissues, vocal cord tissues, and other non-dermal soft tissues. The present method is particularly suitable for the treatment of Gastro-esophageal reflux disease, urinary incontinence, and urinary reflux disease. The method reduces or eliminates immunological response and the rejection of the microspheres. The injection method of the present invention can be carried out by syringes, catheters, needles and other means for injecting or infusing microspheres in a liquid medium. Further, the use of biocompatible, swellable, hydrophilic, non-toxic and substantially spherical microspheres and biocompatible carrier and, preferably, autologous cells, improves tissue acceptance and the effectiveness of the treatment. The methods of the invention also increase connective tissue response.

In one embodiment, the tissue bulking methods of the present invention are for the treatment of Gastro-esophageal reflux disease. This treatment is preferably carried out by injection of the injectable composition into the lower esophageal sphincter or the diaphragm of the mammal in need of treatment. This injection can be facilitated by either endoscopic delivery or by laparoscopic technique. The injection is preferably made into the walls of the sphincter where the esophagus meets the stomach, i.e., the lower esophageal sphincter. This decreases the internal lumen of the sphincter muscle, thus permitting easier contraction of the muscle with reduced regurgitation of the gastric fluids into the esophagus. Furthermore, when combined with the various advantageous embodiments of the injectable composition, such as autologous cells and therapeutic agents, the methods of the present invention provides additional and more beneficial therapeutic effects.

The primary advantages of the method of treating GERD according to the present invention over the prior art methods are:

a) Less invasive effects on the patient compared to surgery;
b) More accurate and effective delivery of the microspheres and therapeutic agents;
c) More permanent effects over antacids or other drugs;
d) Good biocompatibility with chemotactic effects; and
e) Ability to use X-ray visualization or MRI to assist in follow-up evaluation of the patient.

In another embodiment of the present invention, the tissue bulking method is for the treatment of urinary incontinence and urinary reflux disease. This treatment is preferably carried out by injection of the injectable composition into the bladder sphincter or the urethra of the mammal. Treatment according to this method reduces the internal lumen of the sphincter muscle and the urethra muscle, thus permitting easier contraction of the muscle with reduced likelihood of incontinence or urinary reflux. This also reduces the likelihood of bladder-neck hypermobility, which is often a cause for urinary incontinence and urinary reflux disease.

Some of the primary advantages of treating urinary incontinence or urinary reflux disease according to the present invention over prior art methods are:

a) More permanent effect than the use of regular viscous solutions of collagen;
b) More accurate and effective delivery of the microspheres and therapeutic agents;
c) Good biocompatibility with chemotactic effect;
d) Visualization under X-ray or MRI to assist in follow-up evaluation; and
e) Preventing repeated treatments with resorbable naturally occurring substances like collagen.

Injected microspheres can generate some transient adverse reactions such as local inflammation, therefore the microspheres can contain or be injected with anti-inflammatory drugs, such as salicylic acid derivatives including aspirin; para-aminophenol derivatives including acetaminophen; non-steroidal anti-inflammatory agents including indomethacin, sulindac, etodolac, tolmetin, diclodfenac, ketorolac, ibuprofen, naproxen, flurbiprofen, ketoprofen, fenoprofen, oxaprozin; anthranilic acids including mefenamic acid, meclofenamic acid; enolic acids such as piroxicam, tenoxicam, phenylbutazone, oxyphenthatrarone; nabumetone; Vioxx® and Celebrex™. These anti-inflammatories are preferably adsorbed on the microsphere's network and released slowly over a short period of time (a few days). The microspheres may also be used to release other specific drugs which can be incorporated within the microsphere network before injection into the patient. The drug would be released locally at the site of implantation over a short period of time to improve the overall treatment.

The present invention further provides method of tissue bulking by injecting the injectable composition not directly into the body, but extracorporeally into organs, components of organs, or tissues prior to the inclusion of said tissues, organs or components of organs into the body.

The frequency and the amount of injection under the present invention is determined based on the nature and location of the particular tissue defect being treated. Generally, because of the stable and long lasting character of the present invention's injectable composition, multiple injections are not necessary. In certain cases, however, repeated injection may be necessary to achieve optimal results. A skilled practitioner should be able to determine the frequency and the amount of the injection for each particular case.

According to the present invention's methods, after injection, microspheres become secured at the position of the injection. The microspheres are not digested or eliminated by macrophage or other elements of the immune or lymphatic system. Furthermore, the microspheres will not displace or slide away from the position of injection. The secure of the microspheres at the position of injection is due to, among other factors, their size, physical resiliency, and hydrophilicity. The swellability of the microspheres at the site of injection is important in helping secure the microspheres at the site of injection. Upon contacting the physiological fluids and the cells at the site of injection, the microspheres may further swell if there is no pre-injection swelling or the swelling is controlled to a lower level. The physiological condition, including salt concentration (e.g., sodium and potassium) and pH level, may further help the microspheres swell to the desired size.

This property of the microspheres allows precise control of the injection and makes it possible that the microspheres work together at position of injection and provide a scaffold for effective tissue bulking. In fact, the present invention has discovered that, because of the precision of the injection and the securing of the microspheres at the site of injection provided by the invention, it is now possible to create a scaffold of microspheres at the site of injection without forming a scaffold of the microspheres before injection. The "injectable scaffold" of the present invention is especially advantageous over prior art in which surgical procedures are necessary in order to implant a scaffold for certain dermal augmentation. This discovery significantly reduces the complexity of tissue bulking when a scaffold is desired for more effective dermal augmentation in certain cases. This unique contribution of the present invention to tissue bulking and the treatment of GERD, urinary incontinence and urinary reflux disease is made possible, in part, by the well controlled size and degree of swelling of the microspheres, as discussed above. The ability of forming a scaffold at the injection site without forming a scaffold before the injection makes the microspheres of the present invention particularly effective in providing tissue bulking. The size of the scaffold is determined by the amount and frequency of the injection, which is in turn determined by the nature and location of the tissue defects being treated. A skilled practitioner would appreciate the teaching of the present invention as a whole and be able to determine the exact amount and frequency of injection for each particular case.

The injection method of the present invention can be carried out by any type of sterile needles of 18 to 26 gauge and corresponding syringes or other means for injection, such as a three-way syringe. The needles, syringes and other means for injection are commercially available from suppliers such as VWR Scientific Products (West Chester, Pa.), Becton Dickinson, Kendal, and Baxter Healthcare. The size of the syringe and the length of the needle used will dependent on the particular injection based on factors such as the specific disease or disorders being treated, the location and depth of the injection, and the volume and specific composition of the injectable suspension being used. A skilled practitioner will be able to make the selection of syringe and needle based on experience and the teaching of the present invention.

The present invention additionally provides a kit for performing tissue bulking. The kit comprises an 18 to 26 gauge needle and a corresponding syringe, wherein the syringe optionally contains a composition comprising biocompatible, swellable, hydrophilic, non-toxic and substantially spherical microspheres and a biocompatible carrier. The composition is injectable through the needle and the microspheres are not capable of being digested or eliminated by macrophage or other elements of said mammal's immune system. Alternatively, the tissue bulking kit comprises a18 to 26 gauge needle, a corresponding syringe, and separate containers containing the microspheres in dried form and the biocompatible solvent. The dried sterilized microspheres and the solvent are ready to be mixed for injection either in their respective containers or in the syringe. These tissue bulking kits are sterile and ready to use. The kits are designed in various forms based the sizes of the syringe and the needles and the volume of the injectable composition contained therein, which in turn are based on the specific tissue defects the kits are designed to treat.

The invention is further defined by reference to the following examples that describe in detail the preparation of injectable composition and the method of causing tissue bulking using the injectable composition. The following examples are illustrative only and should in no way limit the scope of the present invention. It will be apparent to those skilled in the art that many modifications, both to materials and methods, may be practiced without departing from the purpose and scope of this invention.

5. EXAMPLES

Example 1

In a beaker containing 100 ml of demineralized water, 58 g of sodium chloride and 27 g of sodium acetate are dissolved. One adds 400 ml of glycerol and then the pH is adjusted between 5.9 and 6.1. Then 90 g of N-tris-hydroxy-methyl methylacrylamide, 35 mg of diethylaminoethylacryl-amide and 10 g of N,N-methylene-bis-acrylamide are added. One heats at 60-70 C and 100 mo of a hot 300 mg/ml gelatin solution is added. The total volume of the mixture is adjusted to 980 ml by addition of hot water and then 20 ml of a 70 mg/ml ammonium persulfate solution and 4 ml of N,N,N',N'-tetramethylethylenediamine are added.

This solution is poured into paraffin oil at 50-70 C stirring. After a few minutes, the polymerization reaction of acrylic monomers is manifested by an increase of temperature. The microspheres are then recovered by decanting, washed carefully, screened and sterilized in an autoclave in a buffered medium.

Those microspheres, after screen calibration, possess the characteristics desired for tissue bulking, including a marked cationic charge and an effective adhesion agent (gelatin or denatured collagen).

Example 2

The procedure of Example 1 is followed, using triethylaminoethyl acrylamide instead of diethylaminoethyl acrylamide. After recovery of the spheres, the gelatin is reticulated by means of a 25% glutaraldehyde solution (100 ml of all of the microspheres). The treatment is carried out stirring at 4 C overnight. It is followed by a washing with demineralized water.

Examples 3 and 4

The procedure of Examples 1 and 2 is followed, replacing 10 g of N-tris-hydroxymethyl methylacrylamide with 10 g of acrylic acid. The microspheres obtained possess high swellability that is controllable by salt and ionic concentration and pH level. Those microspheres are advantageously usable in direct view of the user at the time of handling.

Examples 5 and 6

The procedure of Examples 1 and 2 is followed, replacing N-tris-hydroxymethyl methylacrylamide with 10 g of N-acryloyl hexamethylene Procion Red HE-3B. The microspheres obtained possess an intense red coloration due to the integration of the acrylic dye in the polymer lattice. Those microspheres are advantageously usable in direct view of the user at the time of handling.

Examples 7 and 8

One hundred milliliters of microspheres obtained according to Examples 1 to 4 are washed with a 0.1 M borate buffer of pH 8 and then suspended in 50 ml of a 5 mg/ml rhodamine isothiocyanate solution. The suspension is then stirred for at least 15 hours, after which it is washed with a neutral buffer to a colorless supernatant.

Those fluorescent red-colored microspheres are then calibrated and sterilized, and can be used in tissue bulking.

Examples 9 and 10

The procedure of Examples 1 to 4 is followed, replacing 10 g of N-tris-hydroxymethyl methylacrylamide with 10 g of a monomer opaque to X-rays, (acrylamido-3-propionamido)-3-triiodo-2,4,6-benzoic acid.

The microspheres obtained possess the property of absorbing X-rays and are therefore of particular interest in their in vivo follow-up after tissue bulking.

Examples 11 to 14

The procedure of Examples 1 to 2 is followed, adding to the initial monomer solution 5 g of a radio-opaque soluble linear polymer, acrylamino-3-triiodo-2,4,6-benzoic polyacid (Examples 11 and 12) or (acrylamino-3-propionamido)-3-triiodo-2,4,6-benzoic polyacid (Examples 13 and 14).

Those polymers, having a molecular weight exceeding 100,000 Dalton, are imprisoned in the polymer lattice and, without disturbing the general properties of the microspheres for the applications claimed, make it possible to attain a radiopacity usable for the in vivo follow-up of tissue bulking procedure.

Examples 15 and 16

The procedure of Examples 1 and 2 is followed, adding to the initial monomer solution 200 g of barium sulfate power. The microspheres obtained are opaque to both visible light and X-rays.

Examples 17 and 18

The procedure of Examples 1 and 2 is followed, adding 50 mg of magnetite (Fe3O4) to the initial monomer solution.

The microspheres obtained have the property of being detected in (Magnetic Resonance Imaging) MRI imagery.

Example 19

Comparative Evaluation of Two Types of Nonresorbable Spheres

The study consisted of injecting two types of calibrated microspheres, some prepared according to Example 2, the others of polystyrene (Biosilon Nunc Danemark), in pulmonary arterial vascularization of the rat and of observing on days 0, 8 and 30 the extent of the cell reaction and the remodeling modalities of the occluded vessels.

The study revealed four important facts:
placement in suspension and vascular injection of the polystyrene spheres is difficult and clusters are formed at the segmental narrowing constituting the nozzle of the syringe, the base of the catheter and the possible changes of diameter of the catheters;
the cell reaction is earlier, more intense and more durable with the spheres of Example 1 than with polystyrene. On the 8th day the thickness of the cell reaction covering the spheres of the invention is almost three times greater than that covering the polystyrene spheres (34 μm as compared to 13 μm);
there is no differences in kinetics in the vascular remodeling with either material;
no phenomenon suggesting the toxicity of either material was observed.

In conclusion, the microspheres of the invention are more manageable and more effective as adhesive agent.

Example 20

Preparation of Injectable Suspension

A suspension of 100 μm to 120 μm polyacrylamide copolymer microspheres in an oily contrast medium is prepared.

The embodiments of the present invention described above are intended to be merely exemplary and those skilled in the art will recognize, or be able to ascertain using no more than routine experimentation, numerous equivalents to the specific procedures described herein. All such equivalents are considered to be within the scope of the present invention and are covered by the following claims.

The contents of all references described herein are hereby incorporated by reference. Other embodiments are within the following claims.

What is claimed is:
1. A method of tissue bulking in a mammal for the treatment of gastroesophageal reflux disease, comprising inject- ing a composition comprising swellable, biocompatible, hydrophilic, non-toxic and substantially spherical microspheres, having a diameter of about 100 microns to about 300 microns prior to injection, in a biocompatible carrier to said mammal through a needle of about 18 to 26 gauge, wherein the microspheres are non-aggregating and do not clump together, and wherein the microspheres comprise sodium acrylate polymer, acrylamide polymer, acrylamide derivative polymer or copolymer, sodium acrylate and vinyl alcohol copolymer, or mixtures thereof.

2. The method of claim 1, wherein the composition is a suspension of said microspheres in said biocompatible carrier.

3. The method of claim 1, wherein the microspheres swell upon contact with physiological fluids at the injection site.

4. The method of claim 1, wherein diameters of the microspheres after injection are about 1 to about 4 times of diameters of the microspheres immediately prior to injection.

5. The method of claim 1, wherein the polymers comprise from about 0.5% to about 20%, by molecular weight, of crosslinkers.

6. The method of claim 1, which further comprises cells associated with surfaces of at least a portion of the microspheres prior to administration.

7. The method of claim 6, wherein the cells are autologous cells from the subject mammal.

8. The method of claim 7, wherein the autologous cells are fat cells, muscle cells, subcutaneous cells, dermal cells, epidermal cells, or combinations thereof.

9. The method of claim 2, wherein the biocompatible carrier is an emulsion.

10. The method of claim 2, wherein the biocompatible carrier is an organic or a non-aqueous solvent.

11. The method of claim 2, wherein the biocompatible carrier is an aqueous solution, a hydro-organic solution, or mixtures thereof.

12. The method of claim 2, wherein the biocompatible carrier comprises salts composed of cations selected from the group consisting of sodium, potassium, calcium, magnesium, iron, zinc, and ammonium in an amount of from about 0.01 M to about 5 M.

13. The method of claim 12, wherein the salt is supplied in the form of a contrast agent.

14. The method of claim 2, wherein the biocompatible carrier is acylamino-e-propion-amido-3-triiodo-2,4,6 benzoic acid.

15. The method of claim 1, wherein the composition further comprises a therapeutic agent, a radio-pacifying agent, a contrast media, or mixtures thereof.

16. The method of claim 15, wherein said therapeutic agent is bound to the microspheres.

17. The method of claim 1, wherein the injection is into an area of said mammal in need of tissue bulking.

18. The method of claim 1, wherein said composition is injected into a lower esophageal sphincter or diaphragm of said mammal.

19. The method of claim 1, wherein the mammal is a human.

20. The method of claim 1, wherein the administration comprises injecting said composition extracorporeally into organs, components of organs, or tissues prior to their inclusion into said mammal's body, organs, or components of organs.

21. The method of claim 1, wherein the needle has a gauge of about 22 to about 24.

22. The method of claim 1, wherein the biocompatible carrier comprises saline.

23. A method of tissue bulking in a mammal for the treatment of gastroesophageal reflux disease, comprising injecting a composition comprising swellable, biocompatible, hydrophilic, non-toxic and substantially spherical microspheres, having a diameter of about 100 microns to about 300 microns prior to injection, in a biocompatible carrier to said mammal through a needle of about 18-26 gauge, wherein said microspheres comprise a sodium acrylate and vinyl alcohol copolymer.

24. The method of claim 23, wherein the administration comprises injecting said composition into the lower esophageal sphincter or the diaphragm of said mammal.

25. The method of claim 23, wherein diameters of the microspheres after injection are about 1 to about 4 times of diameters of the microspheres immediately prior to injection.

26. A method of tissue bulking in a mammal for the treatment of gastroesophageal reflux disease, comprising injecting a composition comprising swellable, biocompatible, hydrophilic, non-toxic and substantially spherical microspheres, having a diameter of about 100 microns to about 300 microns prior to injection, in a biocompatible carrier to said mammal through a needle of about 18 to 26 gauge, wherein the microspheres comprise sodium acrylate and vinyl alcohol copolymer, N-tris-hydroxymethyl methylacrylamide polymer, diethylaminoethylacrylamide polymer, or N,N-methylene-bis-acrylamide polymer, or mixtures thereof.

* * * * *